(12) United States Patent
Searl

(10) Patent No.: US 10,869,630 B2
(45) Date of Patent: Dec. 22, 2020

(54) SYSTEMS AND METHODS FOR TONGUE-PALATE PRESSURE MEASUREMENT

(71) Applicant: University of Kansas, Lawrence, KS (US)

(72) Inventor: Jeff P. Searl, Overland Park, KS (US)

(73) Assignee: University of Kansas, Lawrence, KS (US)

( * ) Notice: Subject to any disclaimer, the term of this patent is extended or adjusted under 35 U.S.C. 154(b) by 275 days.

(21) Appl. No.: 15/007,022

(22) Filed: Jan. 26, 2016

(65) Prior Publication Data

US 2016/0213306 A1 Jul. 28, 2016

Related U.S. Application Data

(60) Provisional application No. 62/108,358, filed on Jan. 27, 2015.

(51) Int. Cl.
| | |
|---|---|
| *A61B 5/00* | (2006.01) |
| *B29C 39/02* | (2006.01) |
| *B29C 39/38* | (2006.01) |
| *A61B 5/01* | (2006.01) |
| *B29D 99/00* | (2010.01) |
| *A61C 7/08* | (2006.01) |

(52) U.S. Cl.
CPC ............ *A61B 5/4552* (2013.01); *A61B 5/682* (2013.01); *B29C 39/02* (2013.01); *B29C 39/38* (2013.01); *A61B 5/01* (2013.01); *A61B 2562/0247* (2013.01); *A61B 2562/12* (2013.01); *A61C 7/08* (2013.01); *B29D 99/0003* (2013.01)

(58) Field of Classification Search
CPC .......... A61B 5/4552; A61B 2562/0247; A61B 5/682; A61B 5/01; A61B 2562/12; B29C 39/02; B29C 39/38; A61C 7/08
See application file for complete search history.

(56) References Cited

U.S. PATENT DOCUMENTS

| | | | | | |
|---|---|---|---|---|---|
| 4,629,424 | A | * | 12/1986 | Lauks | .................. A61B 5/0002 257/417 |
| 5,212,476 | A | * | 5/1993 | Maloney | ............ A61B 5/04886 340/4.11 |
| 5,553,626 | A | * | 9/1996 | Burger | .................... A61F 5/566 600/587 |
| 5,694,946 | A | * | 12/1997 | Tenerz | .................. A61B 5/032 600/561 |
| 5,706,815 | A | * | 1/1998 | Sarvazyan | ........... A61B 5/0051 600/438 |
| 6,511,441 | B1 | | 1/2003 | Wakumoto et al. | |
| 6,598,006 | B1 | * | 7/2003 | Honda | ...................... A61F 4/00 340/4.11 |
| 6,702,765 | B2 | | 3/2004 | Robbins et al. | |
| 7,047,826 | B2 | * | 5/2006 | Peshkin | .................... G01L 1/14 73/862.53 |
| 7,238,145 | B2 | | 7/2007 | Robbins et al. | |
| 7,438,667 | B2 | | 10/2008 | Robbins et al. | |

(Continued)

*Primary Examiner* — Sean P Dougherty
(74) *Attorney, Agent, or Firm* — Ray Quinney & Nebeker P.C.; Paul N. Taylor

(57) ABSTRACT

A device for measuring the pressure applied between a user's tongue and palate includes a body shaped to fit complimentarily against the user's palate and a pressure sensor affixed to the body such that the device has a total thickness less than 4 millimeters.

19 Claims, 5 Drawing Sheets

(56) References Cited

U.S. PATENT DOCUMENTS

| | | | |
|---|---|---|---|
| 7,890,193 B2 | 2/2011 | Tingey | |
| 8,961,437 B2* | 2/2015 | Al-Tawil | A61B 5/228 600/590 |
| 9,504,417 B2* | 11/2016 | Shimoyama | A61B 5/03 |
| 10,729,372 B2* | 8/2020 | McAuliffe | A61B 5/6847 |
| 2009/0013791 A1* | 1/2009 | Zdeblick | A61B 5/0215 73/700 |
| 2009/0129556 A1* | 5/2009 | Ahn | A61B 6/04 378/208 |
| 2009/0151475 A1* | 6/2009 | Masaki | G01L 1/146 73/862.68 |
| 2010/0204614 A1* | 8/2010 | Lindquist | A61B 5/11 600/586 |
| 2011/0214478 A1* | 9/2011 | Hennig | G01M 7/08 73/12.01 |
| 2012/0123225 A1* | 5/2012 | Al-Tawil | G06F 3/011 600/301 |
| 2012/0172679 A1* | 7/2012 | Logan | A61B 5/01 600/301 |
| 2013/0312655 A1* | 11/2013 | Gravelle | G01K 11/12 116/216 |
| 2014/0343373 A1* | 11/2014 | Shimoyama | A61B 5/03 600/301 |
| 2015/0045698 A1 | 2/2015 | Gribb et al. | |
| 2015/0238142 A1* | 8/2015 | Djordjevski | A61B 5/682 600/587 |
| 2016/0000548 A1* | 1/2016 | Aiden | A61F 2/0059 623/23.72 |
| 2016/0242692 A1* | 8/2016 | McAuliffe | G06F 30/00 |
| 2016/0242951 A1* | 8/2016 | Berk | A61C 7/36 |
| 2017/0265978 A1* | 9/2017 | Borotto | A61C 19/05 |
| 2018/0140252 A1* | 5/2018 | Luxon | A61B 5/03 |
| 2018/0256093 A1* | 9/2018 | Robin | A61F 5/566 |

\* cited by examiner

SYSTEMS AND METHODS FOR TONGUE-PALATE PRESSURE MEASUREMENT

CROSS-REFERENCE TO RELATED APPLICATIONS

The present application claims priority to and the benefit of U.S. Provisional Patent Application No. 62/108,358 filed Jan. 27, 2015 entitled "TONGUE-PALATE SPEECH PRESSURE APPLIANCE", the disclosure of which is incorporated herein by reference in its entirety.

GOVERNMENT RIGHTS

This invention was made with government support under grant numbers DC004960 and TR000001 awarded by the National Institute of Health. The government has certain rights in this invention.

BACKGROUND OF THE DISCLOSURE

Measurement of tongue-palate contact pressure has been of interest to speech (and more recently swallowing) researchers for several decades. The measurement of contact pressure between the tongue and palate aids in the diagnosis of various diseases and conditions. Swallowing disorders (i.e., dysphagia) may be related to activities of the tongue and pressure between the tongue and palate.

The measurement of contact pressure between the tongue and palate also aids in the therapy and treatment of various diseases. A number of medical conditions and communication disorders involve altered tongue function that is addressed through behavioral therapy, usually by a speech-language pathologist, that involves the position, speed and force of tongue movement. For example, speech therapists use tongue-palate pressure measurements to guide the speech therapy of patients developing or regaining the ability to speak. This might include looking at the physical work of the tongue when a person is asked to alter their speech in some manner (e.g., louder-softer, faster-slower, more-less precise), assessing differences in speech production as a function of speaker characteristics (e.g., age, gender, language spoken), or tracking changes in speech production as a function of an independent variable (e.g., disease progression, pharmacological or surgical intervention, time).

Early attempts identified several issues that created problems in obtaining valid pressure measurements. These issues include inappropriate transducer size, inappropriate transducer response characteristics, inefficient and costly pseudopalate construction, and excessive profile of the pseudopalate and transducer.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In an embodiment, a tongue-palate pressure sensing device includes a body, a pressure sensor connected to the body, and a communication module in data communication with the pressure sensor. The body has first surface and a second surface opposite the first surface. The body has a thickness between the first surface and second surface no greater than 4 millimeters.

In another embodiment, a method for manufacturing a tongue-palate pressure sensing device includes heating a base plate, shaping the base plate to form a body of the tongue-palate pressure sensing device, and affixing one or more sensors to the body.

In yet another embodiment, a kit for manufacturing a tongue-palate pressure sensing device includes at least one base plate, at least one pressure sensor, and an adhesive. The base plate includes a body material that is plastically deformable at no greater than 5.0 pounds per square inch of pressure when heated in a range of 38° Celsius to 100° Celsius. The base plate has a thickness of no more than 4 millimeters.

In an even further embodiment, a method of use of a tongue-palate pressure sensing device as described herein. The method may include sending or receiving information from the tongue-palate pressure sensing device. The information may be used to diagnose and/or treat a user.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

One or more specific embodiments of the present disclosure will be described below. These described embodiments are examples of the presently disclosed techniques. Additionally, in an effort to provide a concise description of these embodiments, not all features of an actual embodiment may be described in the specification. It should be appreciated that in the development of any such actual implementation, as in any engineering or design project, numerous embodiment-specific decisions will be made to achieve the developers' specific goals, such as compliance with system-related and business-related constraints, which may vary from one embodiment to another. Moreover, it should be appreciated that such a development effort might be complex and time consuming, but would nevertheless be a routine undertaking of design, fabrication, and manufacture for those of ordinary skill having the benefit of this disclosure.

This disclosure generally relates to devices, systems, and methods for measuring contact pressure between the tongue and the upper palate of a user. A device may be created for and provided to a user that includes one or more sensors thereon. The device may substantially mold to and/or fit against the palate of the user to hold to the palate in a known location and measure one or more conditions during use, including pressure, force, temperature, other types of information, or combinations thereof. For example, a device may include a sensor that measures both pressure and temperature located at a forward edge of a body of the device. In another example, a device may include a sensor substantially longitudinally centered on the device that measures temperature. The device may further include second and third sensors located at the forward and rear edges that each measure pressure.

A method of manufacturing a tongue-palate pressure sensing device may include heating a material such that the material is plastically deformable by a user and/or technician's hands alone. The material may be shaped by the user and/or technician to form a body of the device. One or more sensors may be affixed to the body to measure one or more parameters at a given location on the body.

Figure 1:
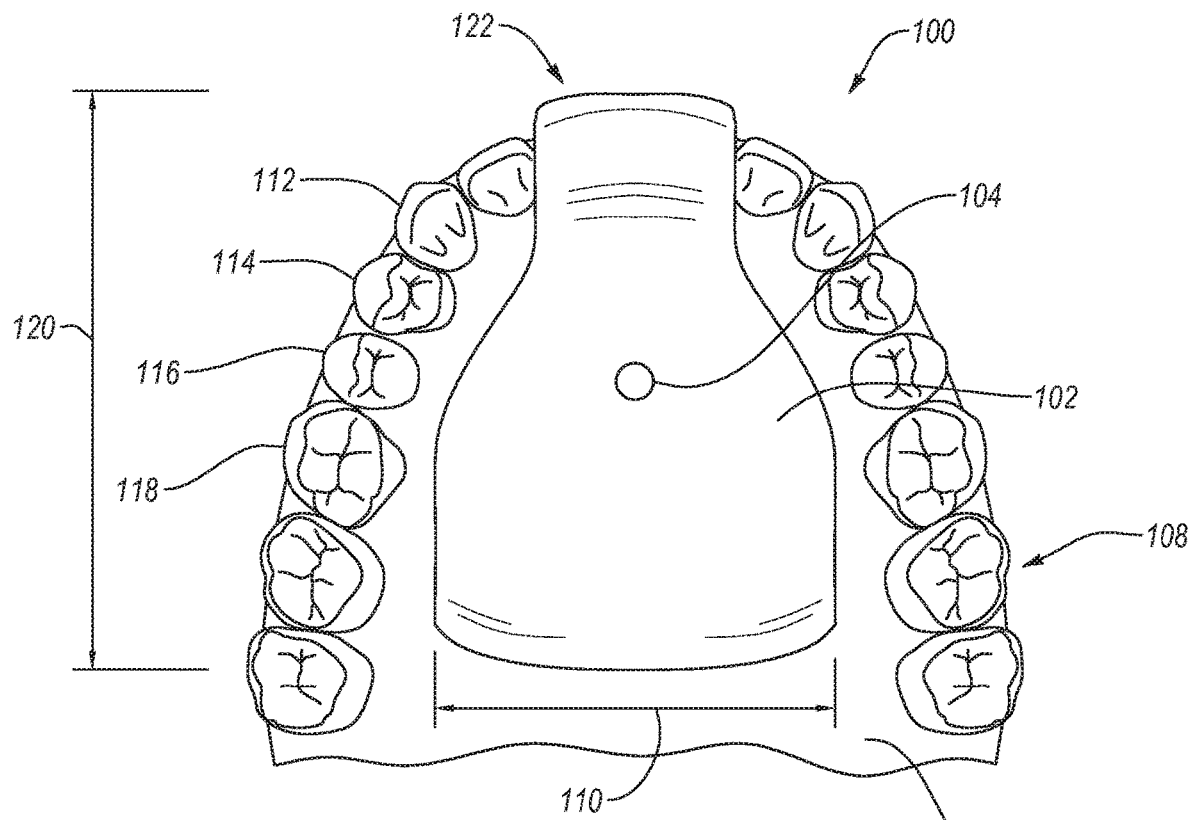
FIG. 1 is a bottom view of an embodiment of a tongue-palate pressure sensing device against the palate of a mouth, according to the present disclosure.

FIG. 1 illustrates an embodiment of a tongue-palate pressure sensing device 100 having a body 102 and a sensor 104 affixed thereto. The tongue-palate pressure sensing device 100 is illustrated in an example application in a user's mouth adjacent the palate 106 and teeth 108. In some embodiments, the body 102 may include or be made of a body material that is molded to and/or moldable to a user's palate 106 and/or teeth 108 (i.e., the body 102 may be a pseudopalate). The body material may include a polymer, a wax, a metal, other material plastically deformable by hand, or combinations thereof. For example, the body 102 may include a single homogeneous body material. In other examples, the body 102 may include a laminar structure of a plurality of body materials. In yet other examples, the body 102 may include a heterogeneous distribution of body materials. In at least one example, the body material may include a base plate wax such as used for dentures or other dental work. The body material may be plastically deformable by hand at a temperature below 100° Celsius and substantially rigid below a temperature of 38° Celsius. For example, the body material may be heated above 38° Celsius and below 100° Celsius such that the body material is substantially moldable to the palate and/or upper teeth of a user. After molding to the palate and/or upper teeth of a user, the body material may then be cooled to below 38° Celsius to form the body 102 of the device 100.

The body 102 may have a width 110 configured to fit against a user's palate 106. For example, the body 102 may have a width 110 in a range have upper and lower values including any of 1.0 centimeters, 1.5 centimeters, 2.0 centimeters, 2.5 centimeters, 3.0 centimeters, 3.5 centimeters, 4.0 centimeters, 4.5 centimeters, 5.0 centimeters, 5.5 centimeters, 6.0 centimeters, or any values therebetween. In some examples, the body 102 may have a width 110 in a range of 1.0 centimeters and 6.0 centimeters. In other examples, the body 102 may have a width 110 in a range of 1.5 centimeters to 5.5 centimeters. In yet other examples, the body 102 may have a width 110 in a range of 2.0 centimeters to 5.0 centimeters.

In some embodiments, the body 102 may have a width 110 configured to fit laterally between a user's cuspid teeth 112. In other embodiments, the body 102 may have a width configured to fit between a user's first bicuspids 114. In yet other embodiments, the body 102 may have a width configured to fit between a user's second bicuspids 116. In further embodiments, the body 102 may have a width configured to fit between a user's first molars 118.

The body 102 may have a length 120. For example, the body 102 may be configured to extend rearward from a user's central incisors 122 a distance along the palate 106. The body 102 may have a length 120 in a range have upper and lower values including any of 1.0 centimeters, 1.5 centimeters, 2.0 centimeters, 2.5 centimeters, 3.0 centimeters, 3.5 centimeters, 4.0 centimeters, 4.5 centimeters, 5.0 centimeters, 5.5 centimeters, 6.0 centimeters, or any values therebetween. In some examples, the body 102 may have a length 120 in a range of 1.0 centimeters and 6.0 centimeters. In other examples, the body 102 may have a length 120 in a range of 1.5 centimeters to 5.5 centimeters. In yet other examples, the body 102 may have a length 120 in a range of 2.0 centimeters to 5.0 centimeters.

In some embodiments, the body 102 may have a length configured to extend from the user's central incisors 122 a distance along the palate 106 to the longitudinal position of the user's cuspid teeth 112. In other embodiments, the body 102 may have a length 120 from the user's central incisors 122 to the user's first bicuspids 114. In yet other embodiments, the body 102 may have a length 120 from the user's central incisors 122 to the user's second bicuspids 116. In further embodiments, the body 102 may have a length 120 from the user's central incisors 122 to the user's first molars 118.

Figure 2:
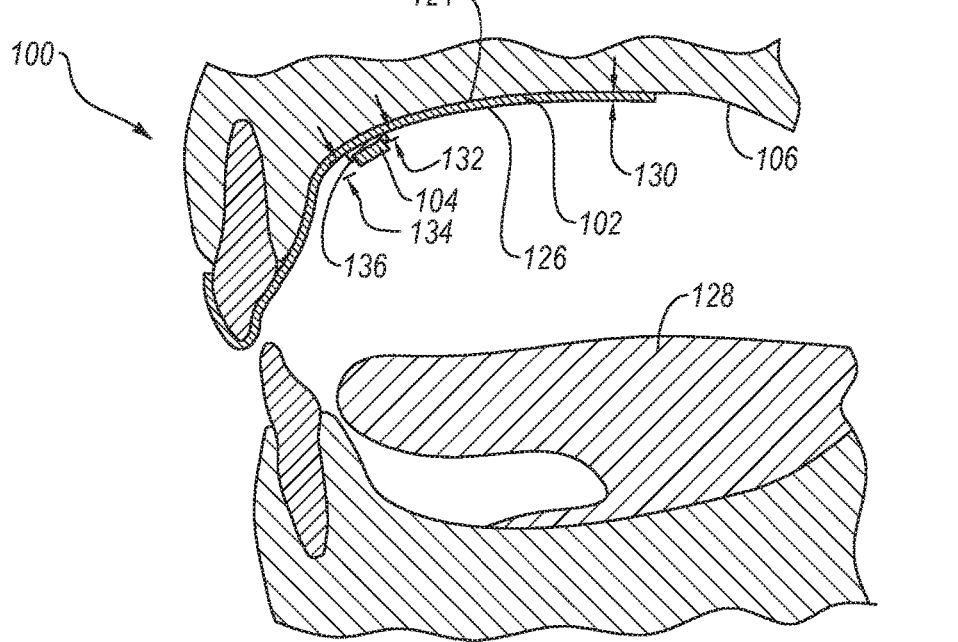
FIG. 2 is a side cross-sectional view of the embodiment of a tongue-palate pressure sensing device of FIG. 1 against the palate of a mouth, according to the present disclosure.

FIG. 2 illustrates a side cross-section of the embodiment of the tongue-palate pressure sensing device 100 of FIG. 1 in a user's mouth. The body 102 may have a first surface 124 and a second surface 126. The first surface 124 may be a generally convex surface configured to be adjacent to the user's palate 106. The second surface 126 may be a generally concave surface oriented away from the user's palate 106 toward the user's tongue 128. The body 102 may have a thickness 130 between the first surface and second surface. In some embodiments, the thickness 130 may be a constant thickness across the body 102. In other embodiments, the thickness 130 may vary over the body 102. For example, the thickness 130 may decrease near an edge of the body 102. In other words, the body 102 may taper toward the edges, which may increase comfort during use for a user. In other examples, the body 102 may have regions with a greater thickness 130 to provide additional strength relative to other portions of the body 102 and regions with a lesser thickness 130 to provide additional flexibility relative to other portions of the body 102.

In some embodiments, the thickness 130 may be in a range having upper and lower values including any of 0.2 millimeters, 0.4 millimeters, 0.6 millimeters, 0.8 millimeters, 1.0 millimeters, 1.5 millimeters, 2.0 millimeters, 2.5 millimeters, 3.0 millimeters, 3.5 millimeters, 4.0 millimeters, or any values therebetween. For example, the thickness 130 may be in a range of 0.2 millimeters to 4.0 millimeters. In other examples, the thickness 130 may be in a range of 0.4 millimeters to 3.5 millimeters. In yet other examples, the thickness 130 may be in a range of 0.6 millimeters to 3.0 millimeters. In at least one example, the thickness 130 may be about 2.0 millimeters.

FIG. 2 illustrates a sensor 104 on the second surface 126 of the tongue-palate pressure sensing device 100 proximate the user's tongue 128. In other embodiments, at least one sensor 104 may be positioned on the first surface 124 of the device 100. In yet other embodiments, at least one sensor 104 may be at least partially within the body 102. In further embodiments, at least one sensor 104 may be entirely within the body 102. In some embodiments, the sensor 104 may have a sensor thickness 132 in a range having upper and lower values including any of 0.2 millimeters, 0.4 millimeters, 0.6 millimeters, 0.8 millimeters, 1.0 millimeters, 1.2 millimeters, 1.4 millimeters, 1.6 millimeters, 1.8 millimeters, 2.0 millimeters, or any values therebetween. For example, the sensor thickness 132 may be in a range of 0.2 millimeters to 2.0 millimeters. In other examples, the sensor thickness 132 may be in a range of 0.4 millimeters to 1.8 millimeters. In yet other examples, the sensor thickness 132 may be in a range of 0.6 millimeters to 1.6 millimeters. In at least one example, the sensor thickness 132 may be no greater than about 1.0 millimeters.

In some embodiments, the total thickness 134 of the device tongue-palate pressure sensing 100 (i.e., of the body 102 and the sensor 104 at the location of the sensor 104) may be in range of 0.2 millimeters, 0.4 millimeters, 0.6 millimeters, 0.8 millimeters, 1.0 millimeters, 1.5 millimeters, 2.0 millimeters, 2.5 millimeters, 3.0 millimeters, 3.5 millimeters, 4.0 millimeters, or any values therebetween. For example, the total thickness 134 may be in a range of 0.2 millimeters to 4.0 millimeters. In other examples, the total thickness 134 may be in a range of 0.4 millimeters to 3.5 millimeters. In yet other examples, the total thickness 134 may be in a range of 0.6 millimeters to 3.0 millimeters. In at least one example, the total thickness 134 may be about 1.0 millimeters.

In some embodiments, a sensor 104 may measure pressure, force, temperature, acidity, other parameters, or combinations thereof. For example, the sensor 104 may measure pressure. In other examples, the sensor 104 may measure both temperature and pressure. In yet other examples, the sensor 104 may measure temperature, pressure, and acidity.

In some embodiments, the sensor 104 may measure pressure applied to the sensor 104 as low as 0.40 kilopascals, as low as 0.35 kilopascals, as low as 0.30 kilopascals, as low as 0.25 kilopascals, or as low as 0.20 kilopascals. In some embodiments, the sensor 104 may measure negative pressures (i.e., suction) applied to the sensor 104. For example, the sensor 104 may measure negative pressure applied to the sensor 104 as low as −0.20 kilopascals, as low as −0.25 kilopascals, as low as −0.30 kilopascals, as low as −0.35 kilopascals, or as low as −0.40 kilopascals.

The sensor 104 may measure a parameter at a frequency in a range having upper and lower values including any of 2.00 kilohertz, 2.25 kilohertz, 2.50 kilohertz, 2.75 kilohertz, 3.00 kilohertz, 3.25 kilohertz, 3.50 kilohertz, 3.75 kilohertz, 4.0 kilohertz, or any values therebetween. In some examples, the sensor 104 may measure a parameter at a frequency between 2.00 kilohertz and 4.00 kilohertz. In other examples, the sensor 104 may measure a parameter at a frequency between 2.5 kilohertz and 3.5 kilohertz. In yet other examples, the sensor 104 may measure a parameter at a frequency about 3.0 kilohertz. In at least one example, the sensor 104 may measure pressure applied to the sensor 104 at a frequency of 2.00 kilohertz to 4.00 kilohertz.

A tongue-palate pressure sensing device 100 may be used to sense tongue-palate pressure for the duration of diagnosis or therapy sessions. A sensor 104 may be stable for at least the duration of a session. For example, a sensor 104 may exhibit substantially no drift in output for at least 10 minutes. In other examples, the sensor 104 may exhibit substantially no drift in output for at least 15 minutes. In yet other examples, the sensor 104 may exhibit substantially no drift in output for at least 20 minutes.

In some embodiments, the sensor 104 may be affixed to the body 102 by a friction fit, a snap fit, a mechanical interlock (e.g., a dovetailed lock), a fastener (e.g., a clip or staple), an adhesive, a pressure differential (e.g., suction), a magnetic force, or combinations thereof. For example, the sensor 104 may be affixed to the body 102 by a portion of the body 102 at least partially overlapping the sensor 104 to hold the sensor 104 in place. In another example, the sensor 104 may be affixed to the body 102 by a friction fit within a recess in the body 102. In yet another example, an adhesive 136 may be applied to the body 102 to further adhere the sensor to the body 102.

In some embodiments, the adhesive 136 may be insoluble in water. For example, the adhesive may include or be a wax. In other embodiments, the adhesive 136 may include or be a dental adhesive. For example, the adhesive 136 may include or be an adhesive for use in adhering dentures or other temporary dental fixtures.

Figure 3:
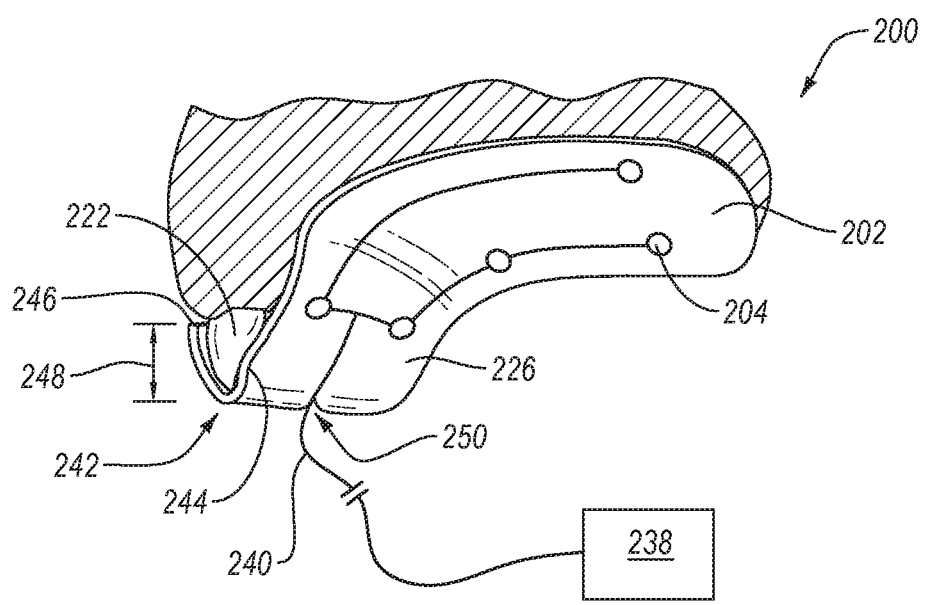
FIG. 3 is a bottom perspective partial cutaway view of an embodiment of a tongue-palate pressure sensing system, according to the present disclosure.

FIG. 3 is a perspective view of another embodiment of a tongue-palate pressure sensing device 200. The tongue-palate pressure sensing device 200 illustrated in FIG. 3 has a plurality of sensors 204 attached to a body 202 in an array to collect information regarding one or more parameters at different locations within a user's mouth. In some embodiments, the array of sensors 204 may include a plurality of the same sensors (e.g., a plurality of pressure sensors). In other embodiments, the array of sensors 204 may include at least one sensor 204 that measures a different parameter from at least one other sensor 204 in the array. For example, the array of sensors 204 may include a pressure sensor and a temperature sensor.

At least one conduit 240 may provide electrical and/or data communication between one or more sensors 204 and a computing device 238. In some embodiments, a conduit 240 may connect one of the sensors 204 and the computing device 238. In other embodiments, the array of sensors 204 may be in electrical and/or data communication with the sensors 204 therein and one conduit 240 may provide electrical and/or data communication between the array and the computing device 238. In yet other embodiments, one or more sensors 204 may be in wireless data communication with a computing device 238.

The computing device 238 may receive a data signal from the array of sensors 204. The computing device 238 may analyze the data signal and/or process the data signal and present one or more values from the data signal to a viewer. In some embodiments, the viewer may be the user, such as during use of the tongue-palate pressure sensing device 200 to provide feedback to the user during speech therapy. In other embodiments, the viewer may be a medical professional, such as during use of the tongue-palate pressure sensing device 200 to provide tongue-palate pressure analysis in diagnosing swallowing disorders (i.e., dysphagia) or other medical conditions. The computing device 238 may present the one or more values to the viewer graphically, numerically, aurally, tactically, by other communication mechanisms, or combinations thereof. For example, the computing device 238 may present a graphical spatial representation (e.g., a map) of the relative pressures applied to the array of sensors 204 by the tongue during speech. In other embodiments, the computing device 238 may present the nominal pressure values recording from each sensor 204 or channel in the array of sensors 204.

The tongue-palate pressure sensing device 200 may have an incisor region 242 that may interact with a user's central incisors 222 (such as those described in relation to FIG. 1). The interaction of the incisor region 242 and the user's central incisors 222 may allow the tongue-palate pressure sensing device 200 to remain substantially stationary relative to the user's mouth during use of the tongue-palate pressure sensing device 200. In some embodiments, the interaction of the incisor region 242 and the user's central incisors 222 may allow the tongue-palate pressure sensing device 200 to remain substantially longitudinally stationary relative to the user's mouth during use of the tongue-palate pressure sensing device 200. In other embodiments, the interaction of the incisor region 242 and the user's central incisors 222 may allow the tongue-palate pressure sensing device 200 to remain substantially laterally (i.e., transverse to the longitudinal direction and in plane with the other teeth) stationary relative to the user's mouth during use of the tongue-palate pressure sensing device 200.

In some embodiments, the incisor region 242 of the device 200 may be integrally formed with the body 202. In other embodiments, the incisor region 242 of the tongue-palate pressure sensing device 200 may be connected to the body 202 by a snap fit, a mechanical interlock (e.g., a dovetailed lock), a fastener (e.g., a clip or staple), an adhesive, a magnetic force, or combinations thereof.

In some embodiments, the incisor region 242 may extend over the incisal surface of the central incisors 222 and the incisor region 242 may include a lingual side 244 and a labial side 246. The labial side 246 of the incisor region 242 may cover a portion of the labial surface of the central incisors 222 in a range having upper and lower values including any of 10%, 20%, 30%, 40%, 50%, 60%, 70%, 80%, 90%, 100%, or any value therebetween. For example, the labial side 246 of the incisor region 242 may cover at least 10% of the labial surface of the central incisors 222. In other examples, the labial side 246 of the incisor region 242 may cover at least 20% of the labial surface of the central incisors 222. In yet further examples, the labial side 246 of the incisor region 242 may cover at least 30% of the labial surface of the central incisors 222.

The labial side 246 may have a labial side height 248 in a range having upper and lower values including any of 2.0 millimeters, 3.0 millimeters, 4.0 millimeters, 5.0 millimeters, 6.0 millimeters, 7.0 millimeters, 8.0 millimeters, 8.0 millimeters, 10.0 millimeters, or any value therebetween. In some examples, the labial side height 248 may be in a range of 2.0 millimeters to 10.0 millimeters. In other examples, the labial side height 248 may be in a range of 3.0 millimeters to 9.0 millimeters. In yet other examples, the labial side height 248 may be in a range of 4.0 millimeters to 7.0 millimeters.

In some embodiments, at least part of the one or more conduits 240 may be routed through a portion of the body 202. For example, speech may include contact of the tongue to a portion of the body 202 adjacent to or near the incisor region 242. The one or more conduits 240 may be at least partially routed through an opening, aperture, or recess in the body 202. The opening, aperture, or recess may allow the one or more conduits 240 to be positioned such the one or more conduits 240 do not protrude or otherwise stand above a second surface 226 of the tongue-palate pressure sensing device 200. For example, a recess 250 may be positioned in the body 202 between two of the user's teeth. The recess 250 may allow the one or more conduits 240 to be directed between two of the user's teeth and may reduce interference with speech due to the one or more conduits 240. In some embodiments, at least a portion of the one or more conduits 240 may be routed between the user's central incisors 222. In other embodiments, the at least a portion of the one or more conduits 240 may be routed between other teeth, such as the cuspids, bicuspids, or molars, or any adjacent combination thereof.

Figure 4:
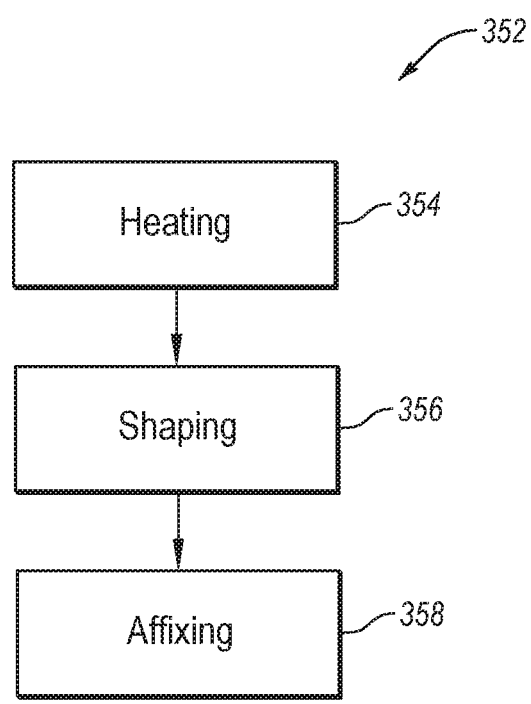
FIG. 4 is a flowchart of an embodiment of a method of manufacturing a tongue-palate pressure sensing device, according to the present disclosure.

FIG. 4 illustrates an embodiment of a method 352 of manufacturing a tongue-palate pressure sensing device according to the present disclosure. The method 352 may include heating 354 a base plate made of or including a plastically deformable body material as described in relation to FIG. 1. Heating 354 the body material base plate to a temperature may allow shaping 356 of the base plate to form a body of a tongue-palate pressure sensing device as described herein. The method 352 may further include affixing one or more sensors to the body. In some embodiments, affixing 358 the one or more sensors may be performed before shaping 356 the base plate to form the body. In other embodiments, affixing 358 the one or more sensors may occur after shaping 356 the base plate. The one or more sensors may be positioned more accurately after shaping 356 the base plate. In some embodiments, affixing the one or more sensors 358 may be performed while the body is in the user's mouth. In other embodiments, the body may be removed from the user's mouth and affixing the one or more sensors 358 may be performed while the body is outside the user's mouth to provide greater access to the body.

Figure 5:
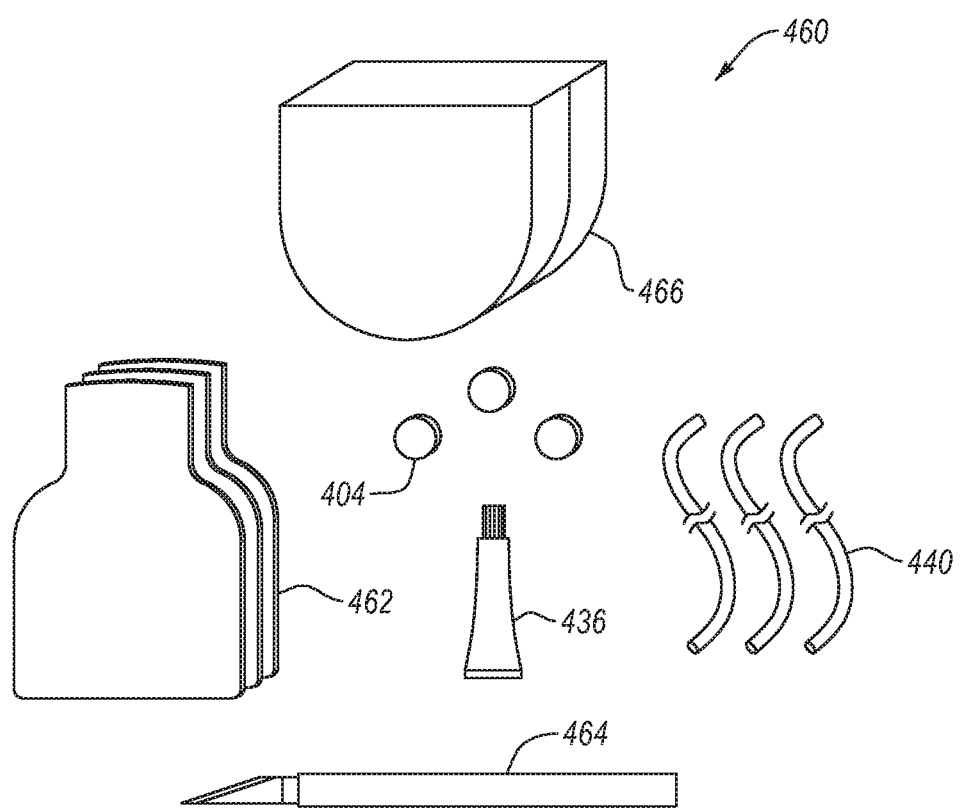
FIG. 5 is a top view of an embodiment of a kit for manufacturing one or more tongue-palate pressure sensing devices, according to the present disclosure.

FIG. 5 illustrates an embodiment of a kit 460 that may be provided for the method described in relation to FIG. 4. Such as shown in FIG. 5, some embodiments of a kit 460 may include one or more base plates 462, one or more sensors 404, and one or more conduits 440. In other embodiments, the kit 460 may further include a container of adhesive 436, a cutting instrument 464 capable of cutting and/or scoring at least the base plate 462, a storage container 466 for storing a formed tongue-palate pressure sensing device, or combinations thereof.

In some embodiments, the base plate 462 may include or be made of a body material as described herein. The body material may be heated during heating of the base plate to a temperature above about 38° Celsius and may be plastically deformable by a user and/or technician's hands. For example, the body material may be heated such that the body material is plastically deformable by the application of 3.0 pounds per square inch of pressure. In other examples, the body material may be heated such that the body material is plastically deformable by the application of 4.0 pounds per square inch of pressure. In yet other examples, the body material may be heated such that the body material is plastically deformable by the application of 5.0 pounds per square inch of pressure.

Figure 6:
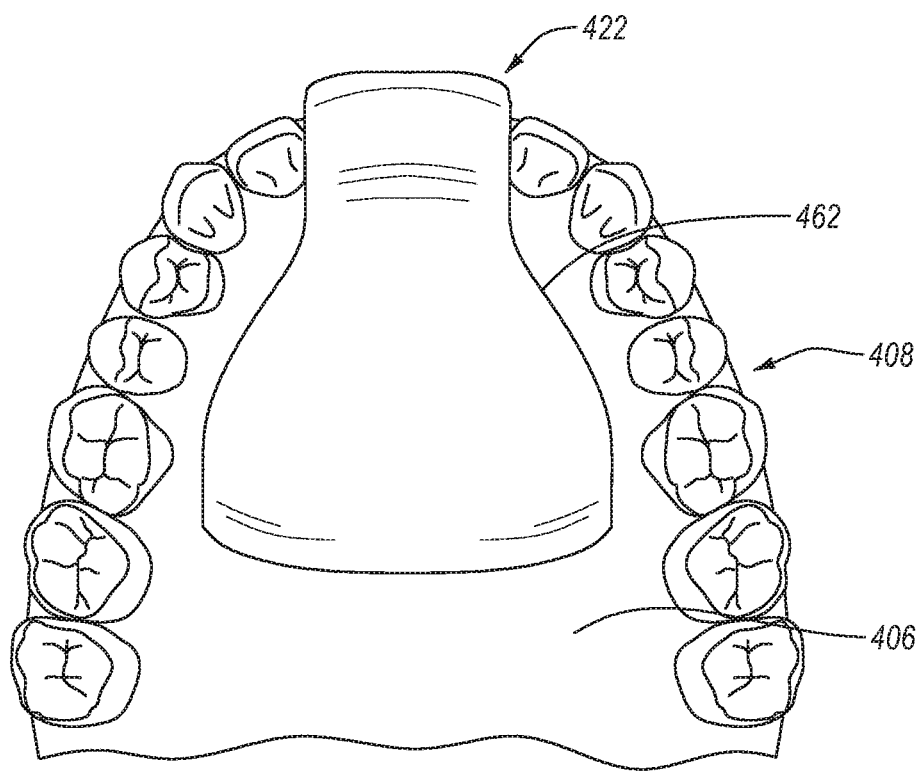
FIG. 6 is a bottom view of the embodiment of a base plate of FIG. 5 formed to a palate, according to the present disclosure.

FIG. 6 illustrates an embodiment of a base plate 462, such as that described in relation to FIG. 5, formed to a user's palate 406. The base plate 462 may be heated prior to forming against the palate 406 by application of direct heat, such as a heat gun, electromagnetic energy (e.g., microwaves), optical energy (e.g., laser), or the base plate 462 may be heated by application of indirect heat. For example, the base plate 462 may be placed in an oven at a predetermined temperature. The base plate 462 may be heated to a temperature in a range having upper and lower values including any of 38° Celsius, 40° Celsius, 42° Celsius, 44° Celsius, 46° Celsius, 48° Celsius, 50° Celsius, 60° Celsius, 70° Celsius, 80° Celsius, 90° Celsius, 100° Celsius, or any values therebetween. For example, the base plate 462 may be heated to a temperature between 38° Celsius and 100° Celsius. In other examples, the base plate 462 may be heated to a temperature between 40° Celsius and 90° Celsius. In yet other examples, the base plate 462 may be heated to a temperature between 42° Celsius and 80° Celsius. In further examples, the base plate 462 may be heated to temperature between 44° Celsius and 70° Celsius.

In some embodiments of the method 352, described in relation to FIG. 4, shaping 356 the base plate 462 shown in FIG. 6 may include cutting and/or trimming of the base plate 462. The base plate 462 may be cut or trimmed to approximate dimensions (e.g., width 110 and length 120, described in relation to FIG. 1) before contouring the base plate 462 to a palate 406 and/or teeth 408. For example, the base plate 462 may initially be oversized for use in the mouth of a user, and the base plate may be reduced in size to allow proper fitting while retaining the base plate 462 to support one or more sensors in the desired locations.

The base plate 462 may be plastically deformable after heating, as described herein, and placed in contact with the palate 406 and at least some of the teeth 408 of the user. In at least one embodiment, the base plate 462 may be placed in contact with the palate 406 and the central incisors 422 and shaped thereto. The base plate 462 may be shaped to the palate 406 by application of pressure to the base plate 462. In some embodiments, the application of pressure may include applying pressure with a user or technician's hands (e.g., fingertip pressure) to urge the base plate 462 against the palate 406. In other embodiments, the application of pressure may include applying pressure with the user's tongue. In yet other embodiments, the application of pressure may include a differential fluid pressure (e.g., suction) created in the user's mouth to draw the base plate 462 against the palate 406. In further embodiments, the application of pressure may include applying pressure with a user- and/or technician-operated tool (e.g., a tongue depressor, an inflatable bladder, a tool having a flat surface, a tool having a curved surface, etc.) to shape the base plate 462 to the palate 406 generally and/or apply force to a specific portion of the base plate 462 to shape the base plate 462 (e.g., a tool having a curved surface to shape the base plate 462 to the lingual side of the central incisors 422). Upon shaping the base plate 462 to the palate 406, the base plate 462 forms at least part of the body of a tongue-palate pressure sensing device, according to the present disclosure.

Figure 7:
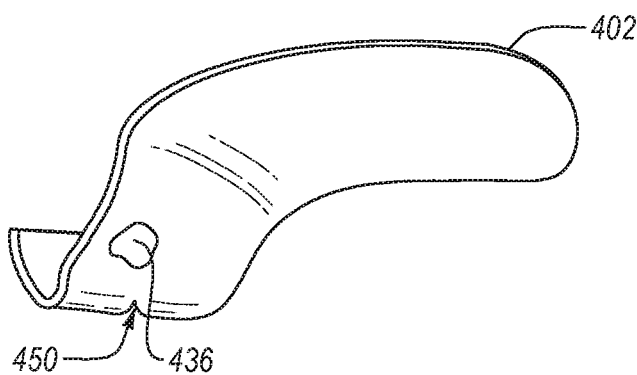
FIG. 7 is a bottom perspective view of the embodiment of a body of FIG. 6, according to the present disclosure.

FIG. 7 illustrates an embodiment of a body 402 after forming the base plate 462 to the palate 406, as described in relation to FIG. 6. As described herein, the body 402 may be shaped to the palate and at least some of the teeth of a user prior to application of one or more sensors to the body 402. In other embodiments, one or more sensors may be applied to the base plate/body 402 prior to shaping the base plate/body 402. In some embodiments, the body 402 may include one or more recesses therein that may limit and/or prevent the movement of the sensor relative to the body 402. In other embodiments, an adhesive 436 may be applied to the body 402 to limit and/or prevent the movement of a sensor relative to the body 402.

In some embodiments, the adhesive 436 may be applied to the body 402 after shaping the body 402. In other embodiments, at least a portion of the body 402 may be scored, hatched, grooved, otherwise roughed, or combinations thereof to increase surface area and/or contact before the adhesive 436 is applied to the body 402. In yet other embodiments, an adhesive 436 may be applied to a recess in the body 402 to limit and/or prevent movement of the sensor relative to the body 402 while reducing the thickness of the body 402 and adhesive 436.

Figure 8:
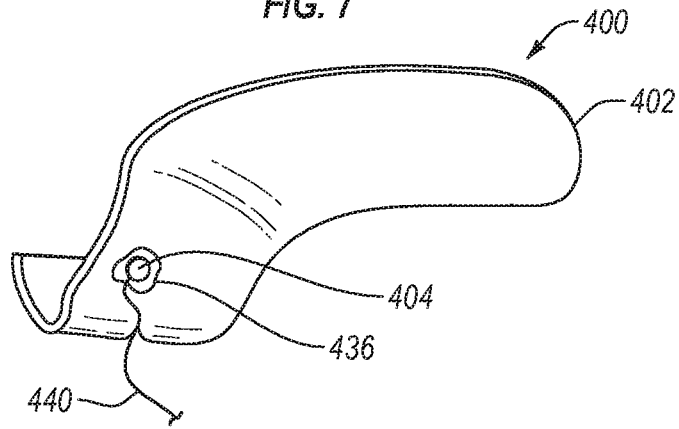
FIG. 8 is a bottom perspective of a tongue-palate pressure sensing device manufactured by the method of FIG. 4, according to the present disclosure.

In some embodiments, an aperture, opening, or recess may be cut into the body 402 for a conduit. FIG. 7 illustrates an example of a recess 450 notched into the body 402 to allow a conduit to be positioned within the recess 450. FIG. 8 illustrates a positioning a conduit 440 in the recess 450. In other embodiments, the recess 450 may extend may have a length sufficient to allow the conduit 440 to be inset into the body 402 to the one or more sensors 404.

FIG. 8 is a bottom perspective view of an embodiment of an assembled tongue-palate pressure sensing device 400 according to the present disclosure. One or more sensors 404 may be affixed to the body 402 of the tongue-palate pressure sensing device 400. In some embodiments, the tongue-palate pressure sensing device 400 may include 1, 2, 3, 4, 5, 6, 7, 8, 9, 10, or more sensors. As described herein, the one or more sensors 404 may measure one or more parameters.

Some embodiments of a tongue-palate pressure sensing device according to the present disclosure may provide users and/or medical professionals with a readily made, economical tongue-palate pressure sensing device that does not interfere with tongue movement and/or swallowing to aide in diagnosis and treatment of a variety of diseases and impairments. A tongue-palate pressure sensing device according the present disclosure may be durable and/or reusable while remaining customizable and modifiable by a user and/or technician.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

I claim:

1. A tongue-palate pressure sensing device configured to engage at least a portion of a labial surface and at least a portion of a lingual surface of one or more of a user's teeth, and at least a portion of said user's palate, the device comprising;
    a body, the body having a first surface and a second surface opposite the first surface, the body having a thickness between the first surface and the second surface, the body being capable of being plastically deformed by an application of a pressure of between 3 pounds per square inch and 5 pounds per square inch at a deformation temperature between 38° C. and 100° C. and incapable of being plastically deformed by an application of between 3 pounds per square inch and 5 pounds per square inch below a rigid temperature of 38° C., the body including:
    a tooth region configured to engage at least said portion of a labial surface and at least said portion of a lingual surface of one or more of said user's teeth; and
    a palate region configured to engage said portion of said user's palate;
    a sensor connected to the body, the sensor configured to operate with less than 5% drift for at least 10 minutes;
    a communication module in data communication with the sensor; and
    at least one conduit providing data communication between the sensor and the communication module, wherein the at least one conduit does not protrude above the second surface.

2. The tongue-palate pressure sensing device of claim 1, further comprising a temperature sensor located on the body.

3. The tongue-palate pressure sensing device of claim 1, wherein the sensor measures both pressure and temperature.

4. The tongue-palate pressure sensing device of claim 2, wherein the sensor is a pressure sensor and the pressure sensor has a sensor thickness no greater than 2 millimeters.

5. The tongue-palate pressure sensing device of claim 4, wherein the device has a total thickness including the thickness of the body and the sensor thickness of no greater than 4 millimeters.

6. The tongue-palate pressure sensing device of claim 1, wherein the sensor is a pressure sensor and the pressure sensor measures pressure applied to the sensor as low as 0.20 kilopascal.

7. The tongue-palate pressure sensing device of claim 1, wherein the sensor is a pressure sensor and the pressure sensor may operate with less than 1% drift for at least 10 minutes.

8. The tongue-palate pressure sensing device of claim 1, further comprising an incisor region having a lingual side and a labial side, the incisor region configured to engage at least one incisor.

9. The tongue-palate pressure sensing device of claim 8, the labial side having a labial side height in a range of 2.0 millimeters to 10.0 millimeters.

10. The tongue-palate pressure sensing device of claim 1, further comprising a plurality of pressure sensors in data communication with the communication module.

11. A method for using a tongue-palate pressure sensing device, the method comprising:
    providing the tongue-palate pressure sensing device of claim 1;
    placing the tongue-palate pressure sensing device of claim 1 in contact with a user's palate; and
    providing data to a computing device using the communication module of claim 1 and the sensor of claim 1.

12. The method of claim 11, wherein the data is provided wirelessly.

13. The method of claim 12, further comprising shaping a base plate by plastically deforming the base plate using a pressure greater than 3.0 pounds per square inch and less than 5.0 pounds per square inch.

14. The method of claim 12, wherein the sensor is affixed to the body by dental adhesive.

15. A tongue-palate pressure sensing device configured to engage at least a portion of a labial surface and at least a portion of a lingual surface of one or more of a user's teeth, and at least a portion of said user's palate, the device comprising;
    a body, the body having first surface and a second surface opposite the first surface, the body being capable of being plastically deformed by an application of a pressure of between 3 pounds per square inch and 5 pounds per square inch at a deformation temperature between 38° C. and 100° C. and incapable of being plastically deformed by an application of between 3 pounds per square inch and 5 pounds per square inch below a rigid temperature of 38° C., the body having a thickness between the first surface and second surface, the body having a tooth region configured to interact with a user's teeth, the body shaped to wrap around at least said portion of a labial surface and at least said portion of a lingual surface of one or more of said user's teeth and extend back onto said portion of said user's palate;

a pressure sensor connected to the body; and a communication module in data communication with the pressure sensor.

16. A tongue-palate pressure sensing device, the device comprising;

a body, the body having first surface and a second surface opposite the first surface, the body having a thickness between the first surface and second surface no greater than 2 millimeters;

a sensor connected to the body, the sensor including both a pressure sensor and a temperature sensor, the sensor having a thickness of no greater than 2 millimeters such that a total thickness including the thickness of the body and the sensor thickness of no greater than 4 millimeters, the sensor capable of measuring pressure applied to the sensor as low as 0.20 kilopascal, and the sensor capable of operating with less than 5% drift for at least 10 minutes, the body being capable of being plastically deformed by an application of a pressure of between 3 pounds per square inch and 5 pounds per square inch at a deformation temperature between 38° C. and 100° C. and incapable of being plastically deformed by an application of between 3 pounds per square inch and 5 pounds per square inch below a rigid temperature of 38° C.; and a communication module in data communication with the sensor; and at least one conduit providing data communication between the sensor and the communication module, wherein the at least one conduit is positioned in a recess between two of said user's teeth.

17. The tongue-palate pressure sensing device of claim 16, wherein the sensor is entirely within the body.

18. The tongue-palate pressure sensing device of claim 15, wherein the body and the tooth region are a unitary piece.

19. The tongue-palate pressure sensing device of claim 16, wherein the at least one conduit is positioned between said user's biscuspids.

* * * * *